US010695232B2

(12) United States Patent
Schmoker et al.

(10) Patent No.: US 10,695,232 B2
(45) Date of Patent: Jun. 30, 2020

(54) ABSORBENT ARTICLE WITH BODY CONFORMING STRUCTURE

(71) Applicant: Kimberly-Clark Worldwide, Inc., Neenah, WI (US)

(72) Inventors: Suzanne Marie Schmoker, Neenah, WI (US); Heidi Bauerlein Hopkins, Neenah, WI (US); Sohyun Sara Park, Neenah, WI (US); Christopher Peter Olson, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 650 days.

(21) Appl. No.: 15/521,802

(22) PCT Filed: Oct. 30, 2014

(86) PCT No.: PCT/US2014/063224
§ 371 (c)(1),
(2) Date: Apr. 25, 2017

(87) PCT Pub. No.: WO2016/068957
PCT Pub. Date: May 6, 2016

(65) Prior Publication Data
US 2017/0246045 A1 Aug. 31, 2017

(51) Int. Cl.
A61F 13/472 (2006.01)
A61F 13/475 (2006.01)
(Continued)

(52) U.S. Cl.
CPC ...... A61F 13/47272 (2013.01); A61F 13/472 (2013.01); A61F 13/4756 (2013.01);
(Continued)

(58) Field of Classification Search
CPC .............. A61F 13/472; A61F 13/47272; A61F 13/4756; A61F 13/535; A61F 13/537; A61F 13/581; A61F 13/625; A61F 2013/530481
See application file for complete search history.

(56) References Cited

U.S. PATENT DOCUMENTS

| 4,631,062 A | 12/1986 | Schultz et al. |
| 4,804,380 A | 2/1989 | Lassen et al. |

(Continued)

FOREIGN PATENT DOCUMENTS

| CN | 1950048 A | 4/2007 |
| CN | 101018523 A | 8/2007 |

(Continued)

Primary Examiner — Kai H Weng
(74) Attorney, Agent, or Firm — Kimberly-Clark Worldwide, Inc.

(57) ABSTRACT

An absorbent article has a top sheet, a back sheet, and an absorbent assembly positioned between the back sheet and the top sheet. The absorbent article includes a fluid intake layer positioned between the absorbent assembly and the top sheet. The fluid intake layer has a rearward-facing arch located in a back portion of the fluid intake layer. The fluid intake layer has an opening. The absorbent article includes a first lateral stiffener and a second lateral stiffener extending along a majority of the longitudinal side edges of the fluid intake layer. The absorbent article includes a first flexure, a second flexure, and a third flexure in a rear portion of the absorbent article.

9 Claims, 8 Drawing Sheets

(51) Int. Cl.
*A61F 13/537* (2006.01)
*A61F 13/535* (2006.01)
*A61F 13/58* (2006.01)
*A61F 13/62* (2006.01)
*A61F 13/53* (2006.01)

(52) U.S. Cl.
CPC .......... *A61F 13/535* (2013.01); *A61F 13/537* (2013.01); *A61F 13/581* (2013.01); *A61F 13/625* (2013.01); *A61F 2013/530481* (2013.01)

(56) References Cited

U.S. PATENT DOCUMENTS

| | | |
|---|---|---|
| 5,171,302 A | 12/1992 | Buell |
| 5,197,959 A | 3/1993 | Buell |
| 5,300,055 A | 4/1994 | Buell |
| 5,439,458 A | 8/1995 | Noel et al. |
| 5,507,735 A | 4/1996 | Van Iten et al. |
| 5,514,104 A | 5/1996 | Cole et al. |
| 5,722,967 A | 3/1998 | Coles |
| 5,919,181 A | 7/1999 | Visscher et al. |
| 6,629,965 B2 | 10/2003 | Drevik et al. |
| 6,932,801 B1 | 8/2005 | Samuelsson |
| 7,166,093 B2 | 1/2007 | Drevik et al. |
| 7,530,973 B2 | 5/2009 | Tanio et al. |
| 7,547,815 B2 | 6/2009 | Ohashi et al. |
| 7,621,899 B2 | 11/2009 | Fujikawa et al. |
| 7,976,525 B2 | 7/2011 | McDaniel |
| 8,016,804 B2 | 9/2011 | Lee |
| 8,048,049 B2 | 11/2011 | Fujikawa et al. |
| 8,157,780 B2 | 4/2012 | Lira et al. |
| 8,211,078 B2 | 7/2012 | Noel |
| 8,231,591 B2 | 7/2012 | Woltman et al. |
| 8,277,428 B2 | 10/2012 | Carvalho et al. |
| 8,343,123 B2 | 1/2013 | Noda et al. |
| 2002/0077613 A1 | 6/2002 | Molas |
| 2002/0177830 A1 | 11/2002 | Fernandez-Kleinlein et al. |
| 2003/0093054 A1 | 5/2003 | Sierri et al. |
| 2003/0097105 A1 | 5/2003 | Chen et al. |
| 2003/0208176 A1 | 11/2003 | Waksmundzki et al. |
| 2004/0018366 A1 | 1/2004 | George et al. |
| 2004/0186449 A1* | 9/2004 | Brisebois .......... A61F 13/53418 604/385.01 |
| 2005/0059942 A1 | 3/2005 | Krautkramer et al. |
| 2005/0148960 A1 | 7/2005 | Price |
| 2005/0148967 A1 | 7/2005 | Baratian et al. |
| 2009/0099539 A1 | 4/2009 | Periman |
| 2012/0053547 A1 | 3/2012 | Schroeder et al. |
| 2012/0277711 A1 | 11/2012 | Kim et al. |
| 2012/0296303 A1 | 11/2012 | Ng et al. |
| 2013/0231628 A1* | 9/2013 | Dieringer .......... A61F 13/47236 604/385.101 |

FOREIGN PATENT DOCUMENTS

| | | |
|---|---|---|
| CN | 101868208 A | 10/2010 |
| CN | 103607990 A | 2/2014 |
| EP | 0 136 524 A1 | 4/1985 |
| EP | 0 681 819 B1 | 12/1998 |
| JP | 4167409 B2 | 10/2008 |
| WO | WO 1999/001095 A1 | 1/1999 |
| WO | WO 2002/045636 A1 | 6/2002 |
| WO | WO 2005/048899 A1 | 6/2005 |
| WO | WO 2011/131020 A1 | 10/2011 |

* cited by examiner

ABSORBENT ARTICLE WITH BODY CONFORMING STRUCTURE

BACKGROUND OF THE INVENTION

Absorbent articles are designed to absorb body fluids while being comfortable to wear but improved leakage protection and increased comfort are ongoing goals. These goals are made more difficult when combined with increased activity of the wearer because pads may not fit and move optimally with the contours and motions of the wearer. Specifically, the back of the pad proximate the wearer's gluteal cleft is one region where fit improvements are needed. Some previous absorbent articles have included a back protection feature in an effort to better conform to the wearer's gluteal cleft. However, these features have not eliminated the bunching, twisting, and/or roping some experience while walking or running. Therefore, there remains a need for an absorbent article that conforms to the body and maintains intimate contact relative to the gluteal cleft with reduced bunching, twisting, and/or roping during increased activity.

SUMMARY OF THE INVENTION

In one aspect, the present invention provides an absorbent article having a top sheet, a back sheet, an absorbent assembly positioned between the back sheet and the top sheet, and a fluid intake layer positioned between the absorbent assembly and the top sheet. The fluid intake layer defines a fluid intake layer length in a longitudinal direction and the absorbent article defines an absorbent article length in the longitudinal direction. The fluid intake layer length is 30-60% the absorbent article length. The fluid intake layer also defines an outer perimeter. The outer perimeter has a rearward-facing arch located in a back portion of the fluid intake layer.

Optionally, the absorbent article includes a first lateral stiffener extending along a first side edge of the fluid intake layer, a second lateral stiffener extending along a second side edge of the fluid intake layer, and a first flexure in a rear portion of the absorbent article wherein the first flexure extends in a direction generally parallel to a longitudinal centerline.

Optionally, the absorbent article includes a first flexure in a rear portion of the absorbent article and extends in a direction generally parallel to a longitudinal centerline. Optionally, the absorbent article includes a second flexure in the rear portion of the absorbent article spaced laterally outward in a first direction from the first flexure. The second flexure defines a first side portion of the absorbent article laterally outward in the first direction from the second flexure. Optionally, the absorbent article includes a third flexure in the rear portion of the absorbent article spaced laterally outward in a second direction from the first flexure. The second direction being opposite the first direction. The third flexure defines a second side portion of the absorbent article laterally outward in the second direction from the third flexure. The second and third flexures define a central portion of the absorbent article there between.

Optionally, the absorbent article includes a first fastener attached to the garment-facing surface of the back sheet in the first side portion and a second fastener attached to the garment-facing surface of the back sheet in the second side portion. Optionally, the central portion of the garment-facing surface of the back sheet is substantially free of fasteners.

Optionally, the second flexure and the third flexure diverge rearward relative to the longitudinal centerline. Optionally, the first flexure, the second flexure, and the third flexure terminate at front points proximate the rearward-facing arch of the fluid intake layer. Optionally, the first flexure, the second flexure, and the third flexure are embossments in the absorbent assembly.

Optionally, the first fastener is a mechanical hook material attached to the garment-facing surface of the back sheet in the first side portion and the second fastener is a mechanical hook material attached to the garment-facing surface of the back sheet in the second side portion.

Optionally, the first fastener is an adhesive attached to the garment-facing surface of the back sheet in the first side portion and the second fastener is an adhesive attached to the garment-facing surface of the back sheet in the second side portion.

Optionally, the fluid intake layer is made of an airlaid material with bi-component fibers and pulp fibers and the rearward-facing arch defines a length dimension in the longitudinal direction of 7-15 mm.

In another aspect, the present invention provides an absorbent article having a top sheet, a back sheet, and an absorbent assembly positioned between the back sheet and the top sheet. The absorbent assembly includes an upper absorbent layer and a lower absorbent layer. The lower absorbent layer is positioned between the upper absorbent layer and the back sheet. A fluid intake layer is positioned between the upper absorbent layer and the top sheet. The fluid intake layer defines an outer perimeter. The outer perimeter has a rearward-facing arch located in a back portion of the fluid intake layer. The fluid intake layer has an opening. The opening defines an inner perimeter. The opening defines a length in a longitudinal direction and the fluid intake layer defines a length in the longitudinal direction, wherein the opening length is 25-75% the fluid intake layer length. The absorbent article includes a first lateral stiffener that is an embossment in the upper absorbent layer and extends along a majority of a first longitudinal side edge of the fluid intake layer. The absorbent article includes a second lateral stiffener that is an embossment in the upper absorbent layer and extends along a majority of a second longitudinal side edge of the fluid intake layer. The absorbent article includes a first flexure that is an embossment in the upper absorbent layer and extends in a direction generally parallel to a longitudinal centerline in a rear portion of the absorbent article.

Optionally, the absorbent article includes a second flexure that is an embossment in the upper absorbent layer in the rear portion of the absorbent article and is spaced laterally outward in a first direction from the first flexure. The second flexure defines a first side portion of the absorbent article laterally outward in the first direction from the second flexure. Optionally, the absorbent article includes a third flexure that is an embossment in the upper absorbent layer in the rear portion of the absorbent article and is spaced laterally outward in a second direction from the first flexure. The first direction is opposite the second direction. The third flexure defines a second side portion of the absorbent article laterally outward in the second direction from the third flexure. The second flexure and the third flexure define a central portion of the absorbent article there between. A first fastener is attached to the garment-facing surface of the back sheet in the first side portion and a second fastener is attached to the garment-facing surface of the back sheet in the second side portion. The garment-facing surface of the back sheet is substantially free of fasteners in the central portion.

Optionally, the first fastener is a mechanical hook material attached to the garment-facing surface of the back sheet in the first side portion and the second fastener is a mechanical hook material attached to the garment-facing surface of the back sheet in the second side portion. Optionally, the first fastener is applied to the garment-facing surface of the back sheet in the first side portion and at an angle relative to the longitudinal centerline and the second fastener is applied to the garment-facing surface of the back sheet in the second side portion and at an angle relative to the longitudinal centerline.

Optionally, the fluid intake layer defines a fluid intake layer length in the longitudinal direction that is 25 to 50% an absorbent article length and the opening defines an opening length in the longitudinal direction that is 40 to 75% the fluid intake layer length.

Optionally, the fluid intake layer defines a fluid intake layer width in a lateral direction, the upper absorbent layer defines an upper absorbent layer length in a longitudinal direction and an upper absorbent layer width in the lateral direction, and the lower absorbent layer defines a lower absorbent layer length in the longitudinal direction and a lower absorbent layer width in the lateral direction. Optionally, the upper absorbent layer width is greater than the lower absorbent layer width, the upper absorbent layer width is greater than the fluid intake layer width, the upper absorbent layer length is greater than the fluid intake layer length, the upper absorbent layer length is greater than the lower absorbent layer length, the fluid intake layer length is less than the lower absorbent layer length, and/or the fluid intake layer width is less than the lower absorbent layer width.

In another aspect, the present invention provides an absorbent article having a top sheet, a back sheet, and an absorbent assembly positioned between the top sheet and the back sheet. The absorbent assembly includes an upper absorbent layer and a lower absorbent layer. The lower absorbent layer is positioned between the upper absorbent layer and the back sheet. The absorbent article includes a fluid intake layer positioned between the upper absorbent layer and the top sheet. The fluid intake layer is positioned in a central portion of the absorbent article and defines an outer perimeter. The outer perimeter has a rearward-facing arch located in a back portion of the fluid intake layer. The rearward-facing arch defines a length in a longitudinal direction of 7-10 mm. The fluid intake layer has an opening, the opening defines a length in the longitudinal direction and the fluid intake layer defines a length in the longitudinal direction, wherein the opening length is 25-75% the fluid intake layer length. A first embossment in the upper absorbent layer extends along a majority of a first side edge of the fluid intake layer, a second embossment in the upper absorbent layer extends along a majority of a second side edge of the fluid intake layer. A first flexure is an embossment in the upper absorbent layer in a rear portion of the absorbent article and extends in a direction generally parallel to a longitudinal centerline. A second flexure is an embossment in the upper absorbent layer in the rear portion of the absorbent article and is spaced laterally outward in a first direction from the first flexure. The second flexure defines a first side portion of the absorbent article laterally outward in the first direction from the second flexure. The second flexure diverges rearward relative to the longitudinal centerline. A third flexure is an embossment in the rear portion of the upper absorbent layer and is spaced laterally outward in a second direction from the first flexure. The first direction is opposite the second direction. The third flexure defines a second side portion of the absorbent article laterally outward in the second direction from the first flexure. The third flexure diverges rearward relative to the longitudinal centerline. The second and third flexures defining a central portion there between. A fastening system is attached to the garment-facing surface of the back sheet. The fastening system covers a majority of a front portion of the garment-facing surface of the back sheet. The fastening system includes a first fastener positioned on the garment-facing surface of the back sheet in the first side portion and a second fastener positioned on the garment-facing surface of the back sheet in the second side portion. The central portion of the garment-facing surface of the back sheet is substantially free of fasteners.

Optionally, the first fastener and the second fastener are continuous hook materials that extend from the front portion through the central portion and into the rear portion.

Optionally, the second flexure includes a first return portion converging rearward at a first angle relative to the longitudinal centerline and the third flexure includes a second return portion converging rearward at a second angle relative to the longitudinal centerline.

Optionally, the first flexure, the second flexure, and the third flexure are embossments in the upper absorbent layer and extend under the fluid intake layer.

Optionally, the absorbent article defines lateral side edges and the absorbent article includes attachment wings extending from the lateral side edges. The first flexure, the second flexure, and the third flexure collectively define front points in the longitudinal direction. The wings define a rear wing position in the longitudinal direction. The rear wing position is closer to the front of the absorbent article than the collective front points.

DETAILED DESCRIPTION OF THE DRAWINGS

The present invention provides an absorbent article that helps maintain intimate contact with the gluteal cleft of the wearer while minimizing bunching, twisting, and roping. The absorbent article of the present invention is constructed to conform to the body by taking and maintaining a raised tent shape in the rear of the article when the wearer moves.

The raised tent shape conforms to the gluteal cleft and moves in response to the alternating movement of the legs thereby helping to isolate the central region and the front region of the pad from the movement of the legs and helping these regions to stay in place for leakage protection and comfort.

Figure 1:
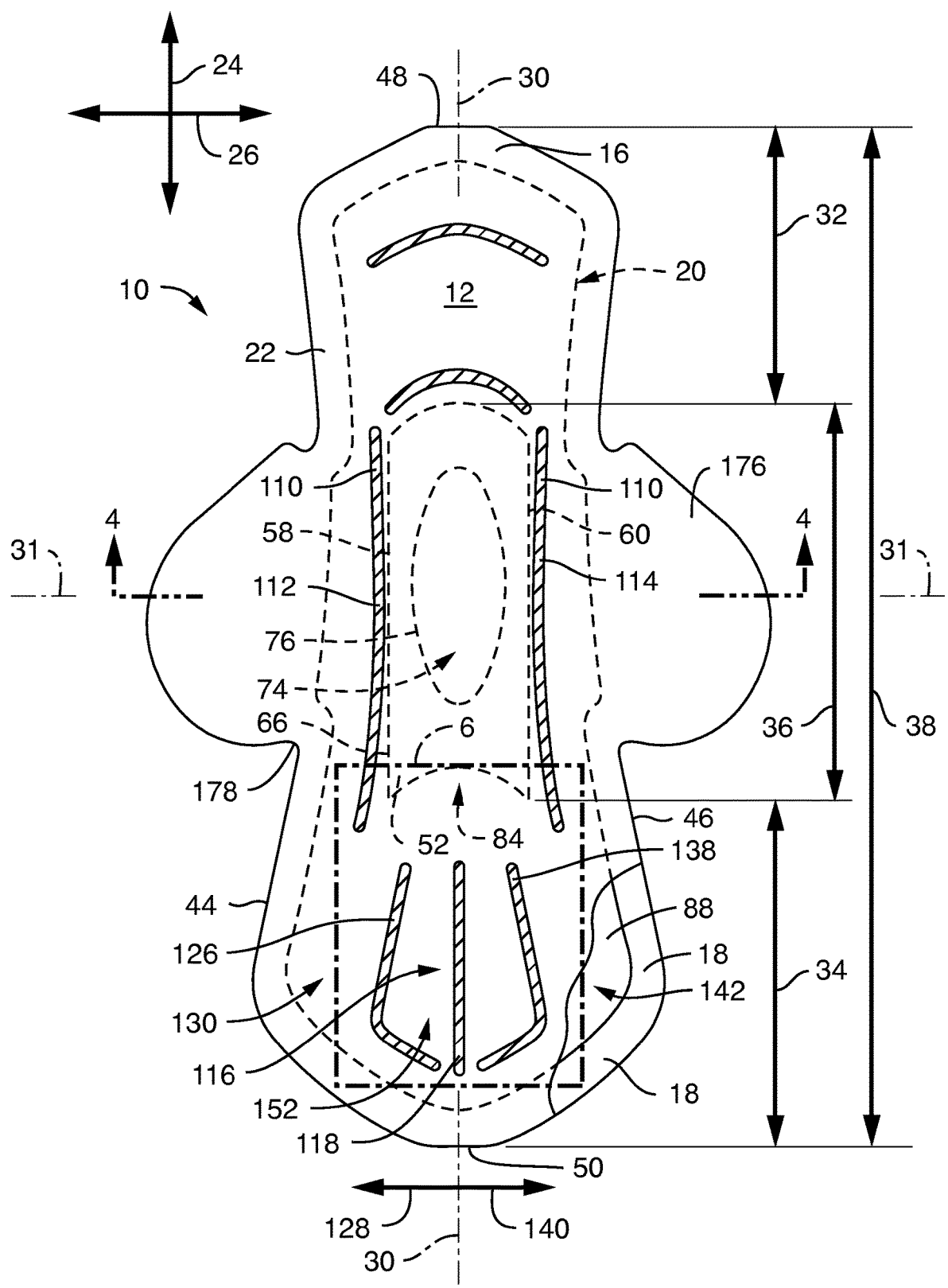
FIG. 1 is a top plan view of the body-facing surface of an exemplary absorbent article of the present invention with portions cut away to illustrate underlying structure.
Figure 2:
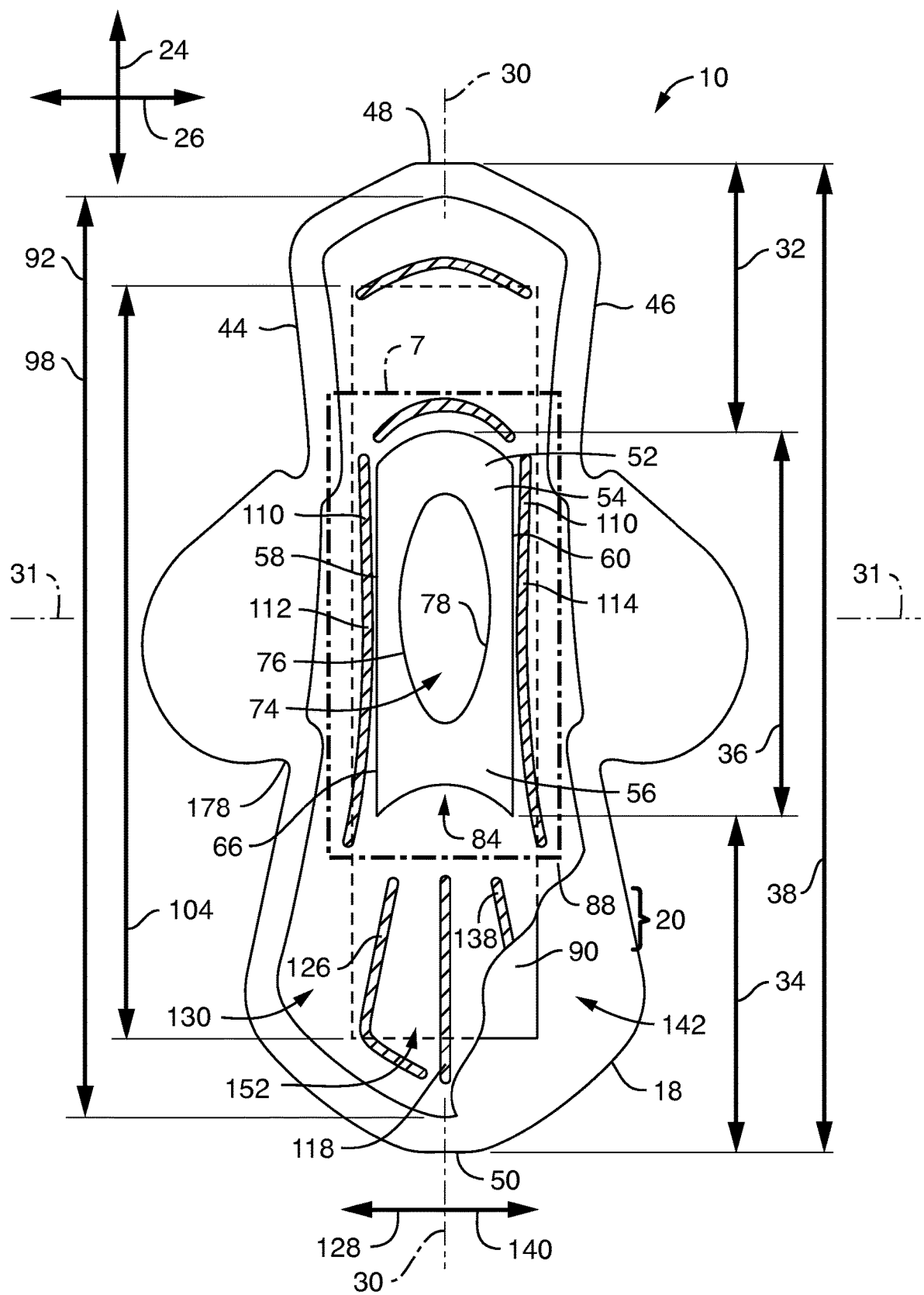
FIG. 2 is a top plan view of the article of FIG. 1 with elements removed and portions cut away to illustrate underlying structure.
Figure 3:
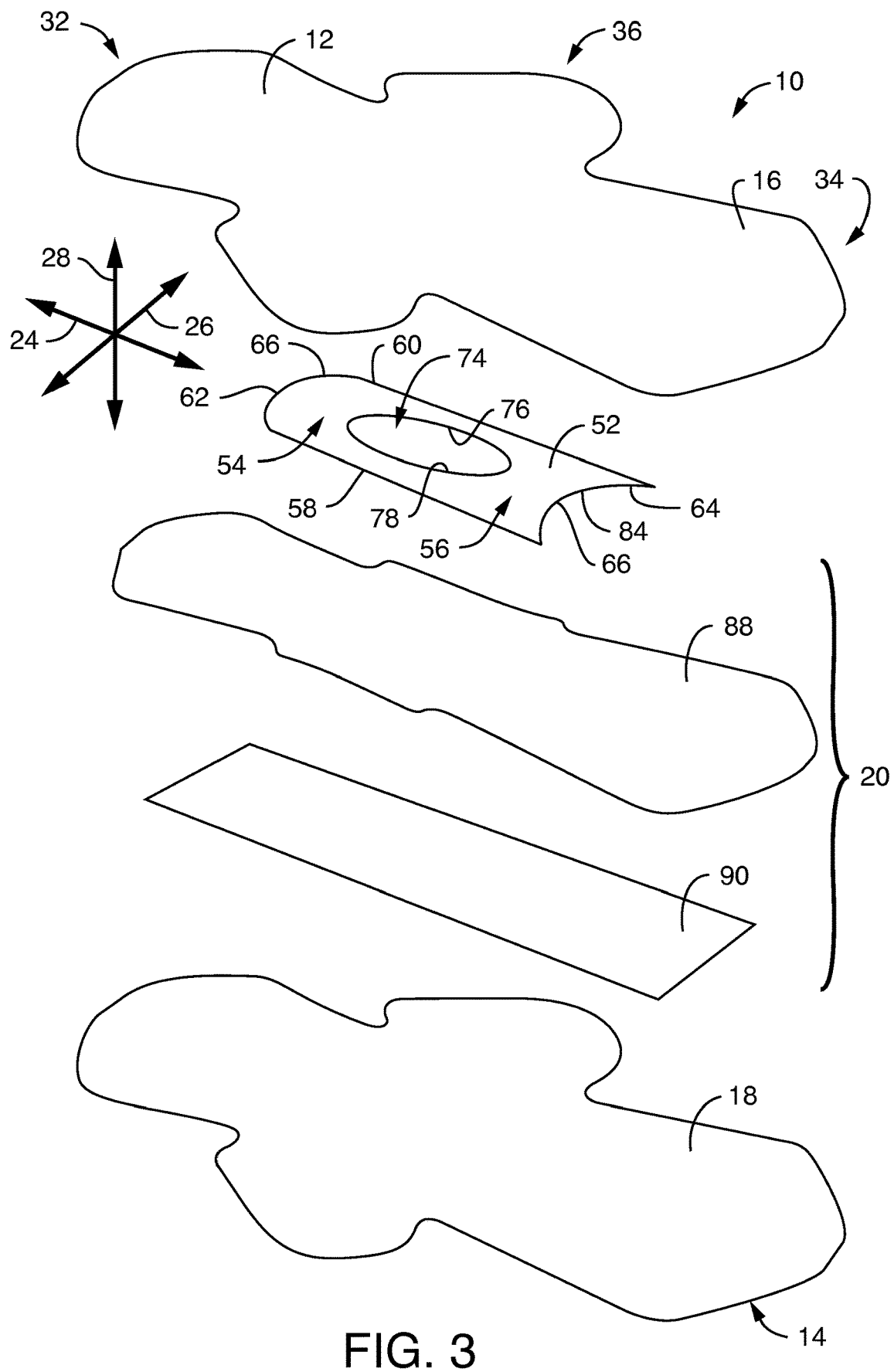
FIG. 3 is an "exploded" perspective view of the absorbent article of FIG. 1 with the elements expanded to better illustrate detail.
Figure 4:
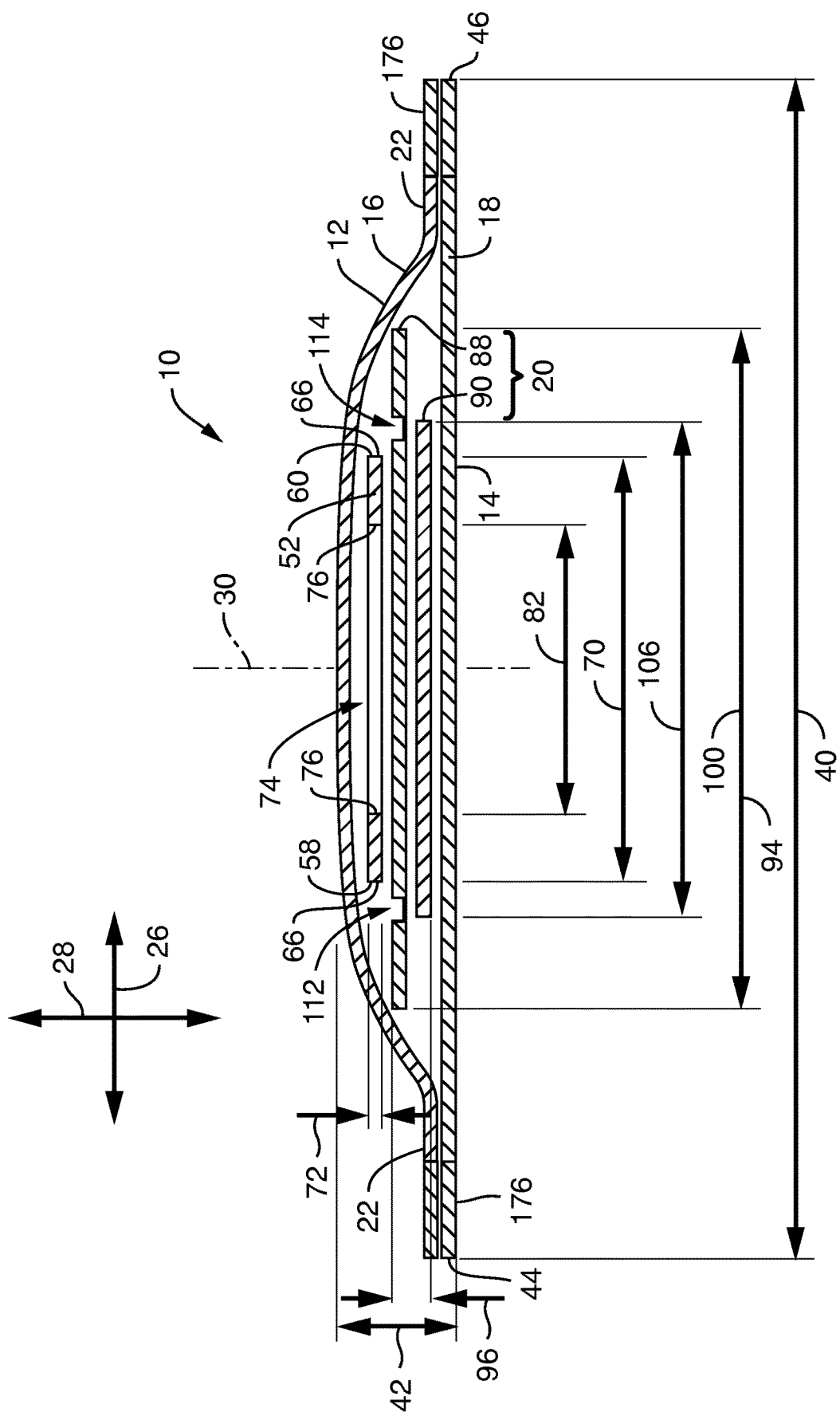
FIG. 4 is a cross-sectional view of the absorbent article of FIG. 1 taken along the line 4-4.
Figure 5:
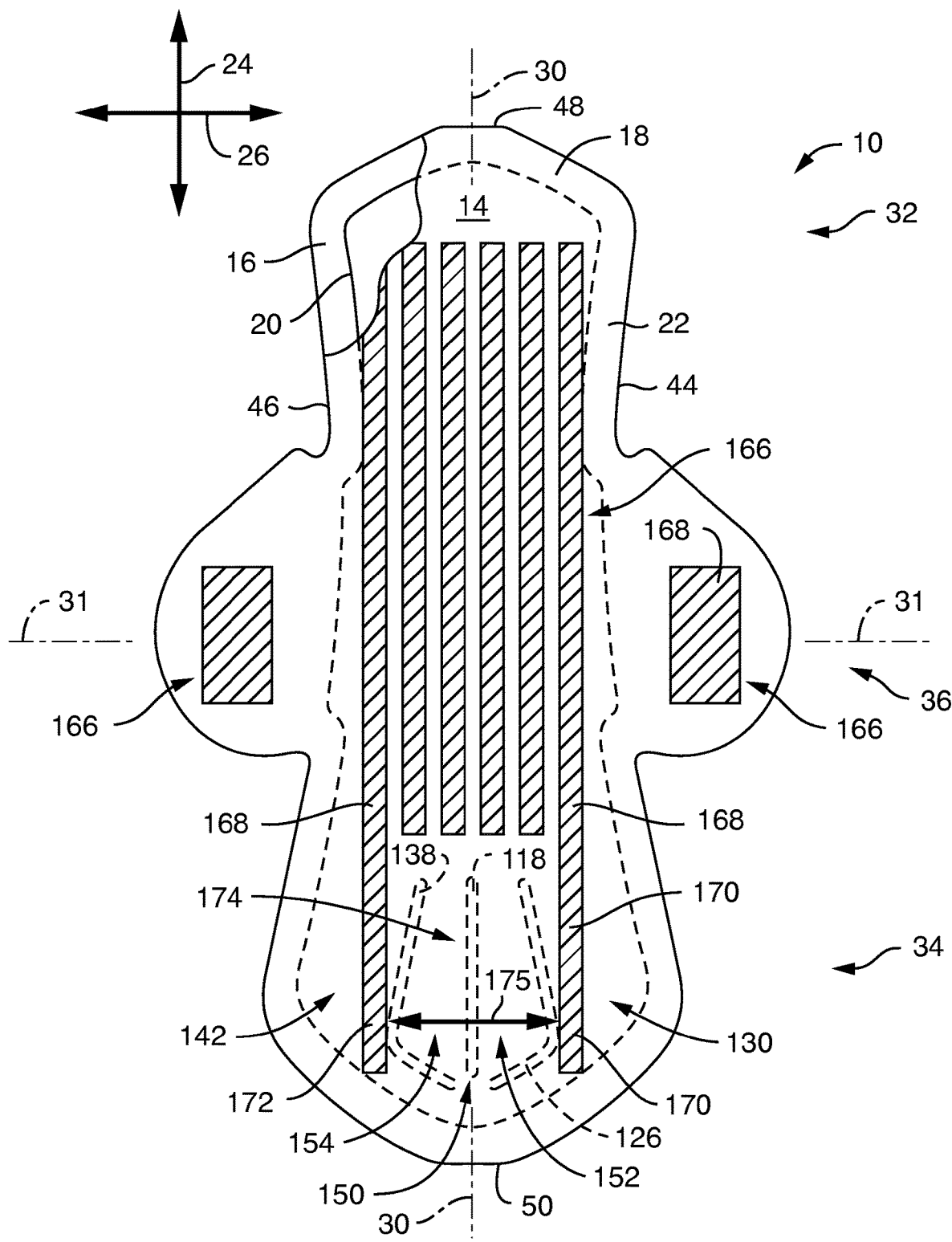
FIG. 5 is a top plan view of the garment-facing surface of the absorbent article of FIG. 1.
Figure 6:
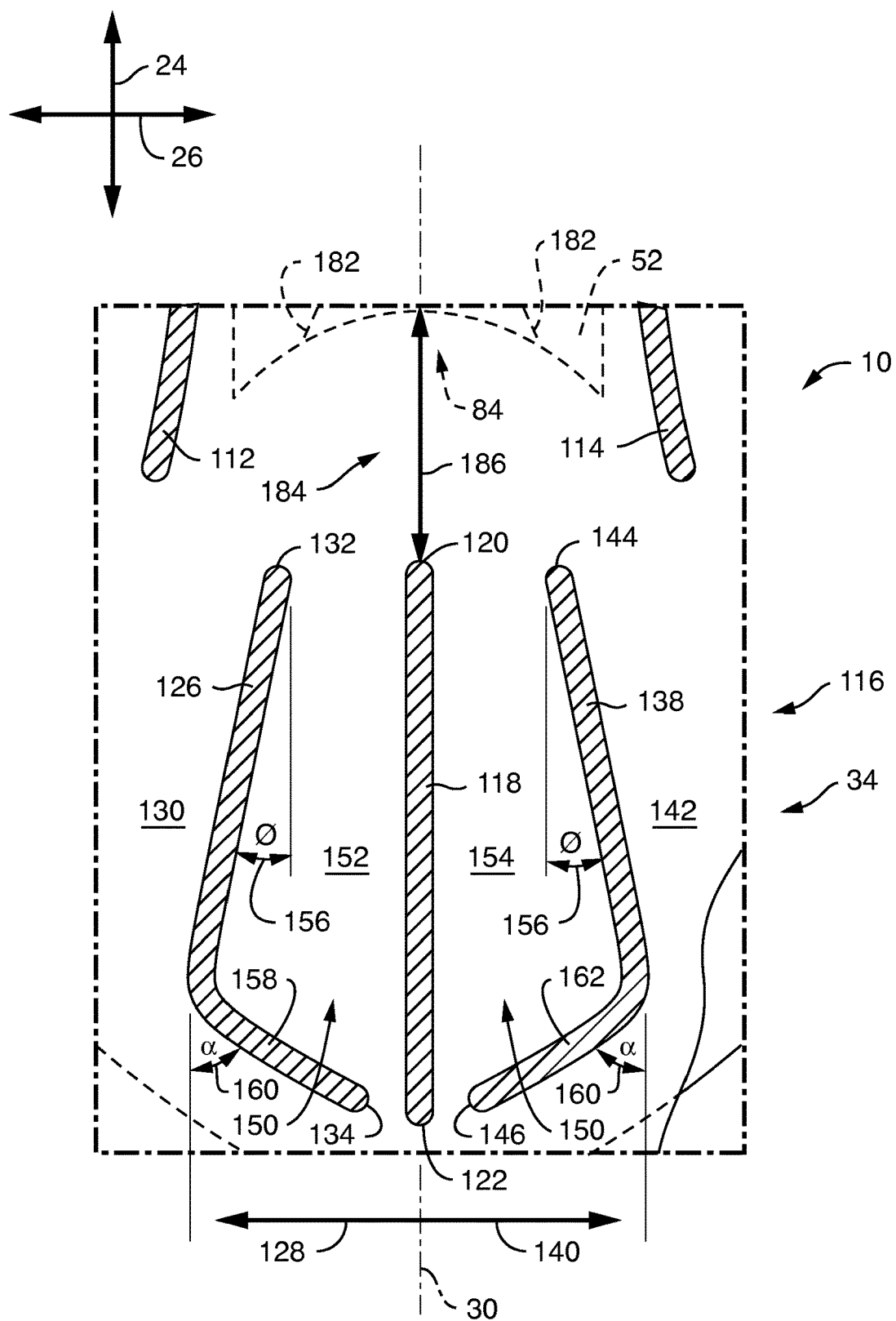
FIG. 6 is a magnified view of the area of FIG. 1 bound by the dot-dash rectangle 6.
Figure 7:
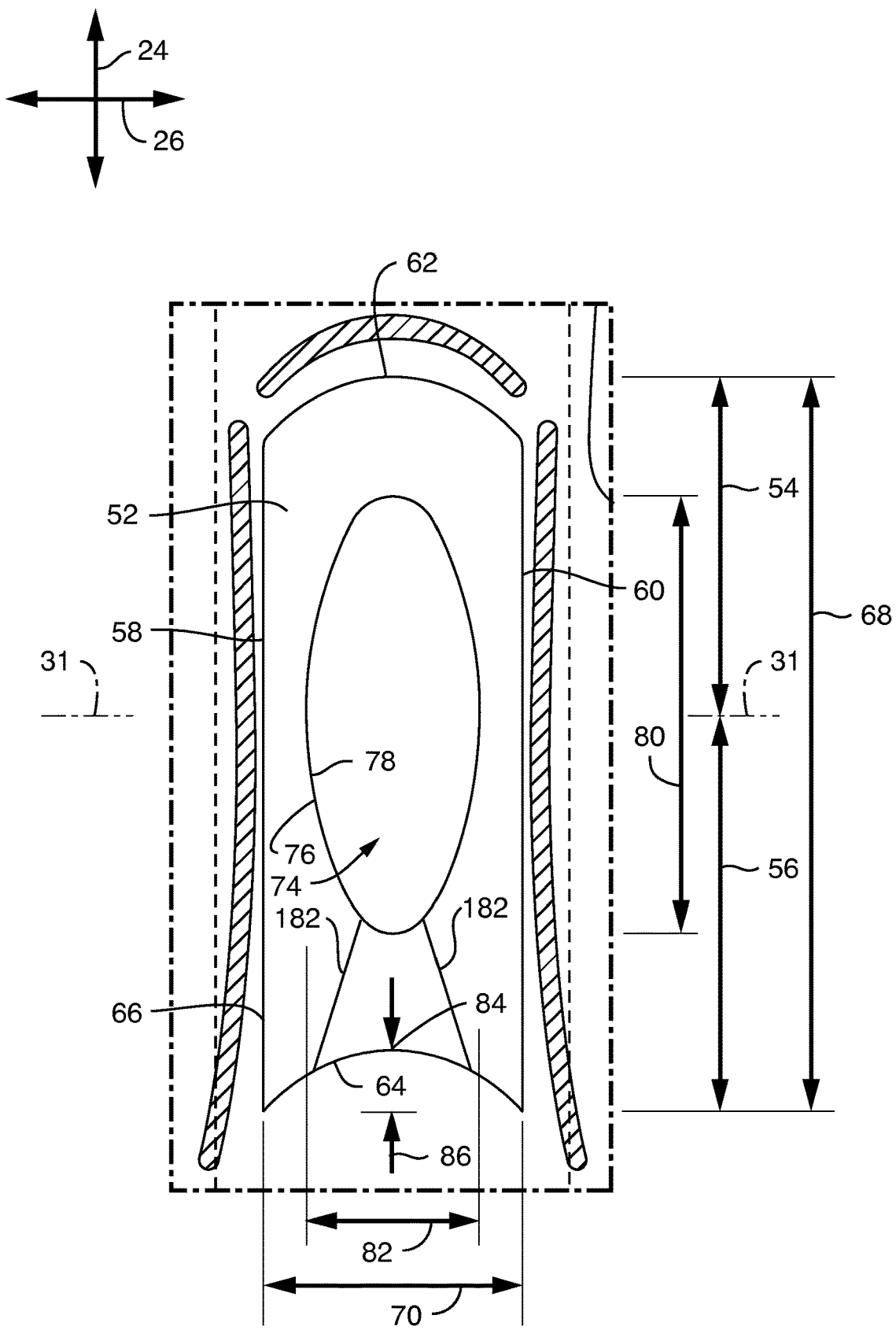
FIG. 7 is a magnified view of the area of FIG. 2 bound by the dot-dash rectangle 7.

Referring now to FIGS. 1-7, an exemplary absorbent article 10 is illustrated in various views and configurations. FIG. 1 is a top plan view of the body-facing surface 12 of the absorbent article 10 with portions cut away to illustrate underlying structure. FIG. 2 is a top plan view of the absorbent article 10 of FIG. 1 with elements removed and portions cut away to illustrate underlying structure. FIG. 3 is an "exploded" perspective view of the absorbent article 10 of FIG. 1 with the elements expanded to better illustrate detail. FIG. 4 is a cross-sectional view of the absorbent article 10 of FIG. 1 taken along the line 4-4. FIG. 5 is a top plan view of the garment-facing surface 14 of the absorbent article 10 of FIG. 1. FIG. 6 is a magnified view of the area of FIG. 1 bound by the dot-dash rectangle 6 to better illustrate details. FIG. 7 is a magnified view of the area of FIG. 2 bound by the dot-dash rectangle 7 to better illustrate details.

The absorbent article 10 includes a top sheet 16, a back sheet 18, and an absorbent assembly 20 positioned between the top sheet 16 and the back sheet 18 as seen in FIG. 3. The top sheet 16 and the back sheet 18 can both extend beyond the absorbent assembly 20 and be bonded together, either entirely or partially, around the periphery using known bonding techniques to form a sealed peripheral region 22 as best illustrated in FIGS. 1 and 4. For example, the top sheet 16 and the back sheet 18 may be bonded together by adhesive bonding, ultrasonic bonding, or any other suitable bonding method, or combinations thereof.

The absorbent article 10 defines a longitudinal direction 24, a lateral direction 26, a thickness direction 28 (also referred to as the Z-direction), a longitudinal centerline 30, and a lateral centerline 31. The absorbent article 10 includes a front portion 32, a rear portion 34, and a central portion 36 extending between the front portion 32 and the rear portion 34. The absorbent article 10 also defines an absorbent article length 38 in the longitudinal direction 24 as illustrated in FIG. 1, an absorbent article width 40 in the lateral direction 26 as illustrated in FIG. 4, and an absorbent article thickness 42 in the thickness direction 28 as illustrated in FIG. 4. The absorbent article includes a first side edge 44, a second side edge 46, a front edge 48 in the front portion 32, and a rear edge 50 in the rear portion 34. In general, the front portion 32 of the article is adapted to be worn towards the front of the wearer, the central portion 36 is adapted to be worn proximate the wearer's crotch, and the rear portion 34 is adapted to be worn towards the rear of the wearer. Optionally, the absorbent article length 38 is 200 to 320 mm, 210 to 280 mm, or 220 to 240 mm. Optionally, the absorbent article width 40, as measured at the lateral centerline 31, is 130 to 160 mm, 135 to 155 mm, or 140 to 150 mm for absorbent articles with wings. Optionally, the absorbent article width 40, as measured at the lateral centerline 31, is 50 to 90 mm, 60 to 80 mm, or 65 to 75 mm for absorbent articles without wings. Optionally, the front portion 32 is defined as the front third of the absorbent article length 38, the central portion 36 is defined as the center third of the absorbent article length 38, and the rear portion 34 is defined as the rear third of the absorbent article length 38.

The top sheet layer 16 defines the body-facing surface 12 of the absorbent article 10 and is adapted to contact the body of the wearer and is liquid permeable to receive body exudates. The top sheet layer 16 is desirably provided for comfort and conformability and functions to direct body exudates away from the body of the wearer, through its own structure, and towards the absorbent assembly 20. The top sheet layer 16 desirably retains little to no liquid in its structure, so that it provides a relatively comfortable, dry, and non-irritating surface next to the skin of the wearer of the absorbent article 10.

The top sheet layer 16 can be a single layer of material, or alternatively, can be multiple layers that are laminated together. The top sheet layer 16 can be constructed of any material such as one or more woven sheets, one or more fibrous nonwoven sheets, one or more film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a top sheet layer.

In various embodiments, the top sheet layer 16 can be constructed from various nonwoven webs such as meltblown webs, spunbond webs, hydroentangled spunlace webs, or through air bonded carded webs. Examples of suitable top sheet layer materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials.

In various embodiments, the top sheet layer 16 may contain a plurality of apertures (not shown) formed therethrough to permit body exudates to pass more readily into the absorbent assembly 20. The apertures may be randomly or uniformly arranged throughout the top sheet. The size, shape, diameter, and number of apertures may be varied to suit various needs.

Optionally, the top sheet 16 can have a basis weight ranging from about 5, 10, 15, 20 or 25 gsm to about 50, 100, 120, 125 or 150 gsm. For example, in an embodiment, a top sheet 16 can be constructed from a through air bonded carded web having a basis weight ranging from about 15 gsm to about 100 gsm. In another example, a top sheet layer 16 can be constructed from a through air bonded carded web having a basis weight from about 20 gsm to about 50 gsm, such as a through air bonded carded web that is readily available from nonwoven material manufacturers.

Optionally, the top sheet layer 16 can be at least partially hydrophilic. In various embodiments, a portion of the top sheet layer 16 can be hydrophilic and a portion of the top sheet layer 16 can be hydrophobic. In various embodiments, the portions of the top sheet layer 16 which can be hydrophobic can be either an inherently hydrophobic material or can be a material treated with a hydrophobic coating.

In various embodiments, the top sheet layer 16 can be a multicomponent top sheet layer such as by having two or more different nonwoven or film materials, with the different materials placed in separate locations in the transverse direction of the absorbent article 10 (not shown). For example, the top sheet layer 16 can be a two-layer or multi-component material having a central portion positioned along and straddling the longitudinal centerline of the absorbent article, with lateral side portions flanking and bonded to each side edge of the central portion (not shown).

The central portion can be constructed from a first material and the side portions can be constructed from a material which can be the same as or different from the material of the central portion. In such embodiments, the central portion may be at least partially hydrophilic and the side portions may be inherently hydrophobic or may be treated with a hydrophobic coating. Examples of constructions of multi-component top sheet layers are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

The absorbent article 10 also includes a liquid permeable fluid intake layer 52 positioned in the Z-direction 28 between the top sheet layer 16 and the absorbent assembly 20 as seen in FIG. 3. The relative position of the fluid intake layer 52 in the longitudinal direction 24 and the lateral direction 26 is illustrated in FIG. 2. FIG. 2 is the absorbent article 10 of FIG. 1 but with the top sheet layer 16 removed to better illustrate underlying structure. Additionally, details of the fluid intake layer 52 can be seen in FIG. 7, which is a magnified view of the area of FIG. 2 bound by the dot-dash rectangle 7. The fluid intake layer 52 includes a front portion 54 and a rear portion 56 which are defined, in part, by the lateral centerline 31. The front portion 54 of the fluid intake layer 52 is positioned between the lateral centerline 31 and the front edge 48 of the absorbent article 10. The rear portion 56 of the fluid intake layer 52 is positioned between the lateral centerline 31 and the rear edge 50 of the absorbent article 10.

The fluid intake layer 52 defines a first side edge 58, a second side edge 60, a front end edge 62, and a rear end edge 64. The first side edge 58, the second side edge 60, the front end edge 62, and the rear end edge 64 collectively define the fluid intake layer perimeter 66. The fluid intake layer 52 can be made of a material that can rapidly transfer, in the Z-direction 28, body exudates that are delivered to the top sheet layer 16. The fluid intake layer 52 can generally have any shape and/or size desired. Optionally, the fluid intake layer 52 can have a generally rectangular shape, with a length 68 (FIG. 7) equal to or less than the overall length 38 (FIG. 1) of the absorbent article, and a width 70 less than the width 40 of the absorbent article 10 (FIG. 4). Optionally, the fluid intake layer 52 can have a length 68 of about 70 to 120 mm, 80 to 110 mm, or 90 to 100 mm and a width 70, at the lateral centerline 31, of about 20 to 40 mm, 25 to 35 mm, or 30 to 35 mm (FIG. 7). Optionally, the fluid intake layer length 68 is 25 to 60%, 25 to 50%, or 25 to 40% the absorbent article length 38. Optionally, the fluid intake layer 52 thickness 72 in the Z-direction 28 is from about 0.5 mm to about 3 mm.

Any of a variety of different materials can be used for the fluid intake layer 52 to accomplish the above-mentioned functions. The material may be synthetic, cellulosic, or a combination of synthetic and cellulosic materials. The fluid intake layer 52 can be constructed from any woven or nonwoven material. For example, the fluid intake layer 52 can be constructed as an airlaid or TABCW material. For example, airlaid cellulosic fibers may be suitable for use in the fluid intake layer. The airlaid cellulosic fibers may have a basis weight ranging from about 10 or 100 gsm to about 250 or 300 gsm. The airlaid cellulosic fibers can be formed from hardwood and/or softwood fibers. An airlaid cellulosic fiber material can have a fine pore structure and can provide an excellent wicking capacity, especially for menses. Optionally, a fluid intake layer 52 may be a TABCW material laminated with an airlaid material where the TABCW/airlaid laminate has a basis weight of 125 gsm to 168 gsm, a thickness of 1.7 mm to 2.8 mm, and a density of about 0.06 g/cc. The TABCW portion of this laminate may include polyethylene fibers, polypropylene fibers, polyester fibers, polyethylene/polypropylene bi-component fibers, or combinations thereof. The airlaid portion of this laminate may include fluff pulp fibers and about 15-20% bi-component fibers by weight. Optionally, a fluid intake layer 52 may be a coform material having a basis weight of 157 to 202 gsm, a thickness of 2.2 to 2.6 mm, and a density of about 0.08 g/cc. This coform material may include fluff pulp fibers and about 31% bi-component fibers by weight. The bi-component fibers may be polypropylene fibers. This coform material may be formed on a spunbond carrier sheet. Optionally, a fluid intake layer 52 may be a thermally bonded web having a basis weight of about 125 to 160 gsm, a thickness of 2.25 to 2.75 mm, and a density of about 0.06 g/cc. This thermally bonded material may include fluff pulp fibers and about 21% bi-component fibers by weight. The bi-component fibers may be polypropylene fibers.

Additionally, to further enhance the ability of the absorbent article 10 to transfer body exudates in the Z-direction 28 from the top sheet layer 16 toward any lower layers in the absorbent article 10 as well as to enhance the ability of the fluid intake layer 52 to conform to the wearer's body based on its ability to bend, the fluid intake layer 52 can optionally have an opening 74 as illustrated in FIGS. 2 and 7. The opening 74 can have any suitable shape, such as ovular, circular, rectangular, square, triangular, etc. In various embodiments, the opening 74 in the fluid intake layer 52 can be elongated and can be oriented in the longitudinal direction 24 of the absorbent article 10. The opening 74 in the fluid intake layer 52 can be bounded by a perimeter 76 which can form an inner edge 78 of the fluid intake layer 52.

The opening 74 can be located at various positions along the longitudinal direction 24 and the lateral direction 26 of the fluid intake layer 52 depending upon the primary location of body exudate intake or the purpose for which the absorbent article 10 is being used. For example, in various embodiments, the fluid intake layer 52 and the opening 74 in the fluid intake layer 52 can be positioned so that it is in substantial alignment with the longitudinal centerline 30 and the lateral centerline 31 of the absorbent article 10 as illustrated in FIG. 2. This allows the opening 74 to be centrally disposed so that it can be positioned below the main point of body exudate discharge and so that it can act as the primary body exudate receiving area for the absorbent article 10. However, centralized positioning of the fluid intake layer 52 and the opening 74 of the fluid intake layer 52 is not required, and in various embodiments, depending on the primary location where body exudate intake might occur, the fluid intake layer 52 and the opening 74 of the fluid intake layer 52 may be substantially aligned with the longitudinal centerline 30 only.

As best seen in FIG. 7, the opening 74 in the fluid intake layer 52 can optionally have a longitudinal length 80 from about 40 to 70 mm, 50 to 60 mm, or 53 to 57 mm and can optionally have a lateral width 82 from about 15 to 30 mm, 20 to 25 mm, or 21 to 23 mm. The opening 74 in the fluid intake layer 52 can be defined by the perimeter 76 and can optionally have a length 80 that is from about 15, 20 or 25% to about 70, 75, or 80% of the overall longitudinal length 68 of the fluid intake layer 52. The opening 74 in the fluid intake layer 52 can be defined by the perimeter 76 and can have a width 82 that can optionally be from about 20, 25 or 30% to about 70, 75 or 80% of the width 70 of the fluid intake layer 52. The opening 74 in the fluid intake layer 52 can serve to funnel and direct body exudates from the top sheet layer 16 and towards lower layers of the absorbent article 10 in the depth (Z) direction 28. The opening 74 in the fluid intake layer 52 can also form a cup or well-like structure for holding body exudates and preventing its leakage away from a central region of the absorbent article 10 and towards the edges of the absorbent article 10.

Additionally, the fluid intake layer 52 has a rearward-facing arch 84 located along the rear end edge 64 of the fluid intake layer 52. The rearward-facing arch 84 is believed to enhance the ability of the absorbent article 10 to form an upward tented configuration in the rear portion 34 as discussed in more detail below. The rearward-facing arch 84 is also believed to enhance the ability of the fluid intake layer 52 to conform to the wearer's body based on its ability to bend. The rearward-facing arch 84 defines a maximum length 86 in the longitudinal direction 24. The maximum length 86 may optionally be 5 to 40 mm, 6 to 30 mm, 7 to 20 mm, or 8 to 10 mm. Optionally, the maximum length 86 of the rearward-facing arch 84 may be located proximate the longitudinal centerline 31 as illustrated in FIG. 7. Optionally, the maximum length 86 of the rearward-facing arch 84 may be generally aligned with the flexures as described in more detail below.

Optionally, the fluid intake layer 52 may further include one or more haunches 182. The haunches 182 may be created by embossing, perforating, bonding, scoring, or otherwise manipulating the fluid intake layer 52. The haunches 182 are believed to improve body conformance. The haunches 182 may also work in conjunction with the other structure of the absorbent article 10 to help initiate and/or maintain the raised tenting configuration in the rear portion 34. The haunches 182 may be generally aligned with one or more flexures as described in more detail below.

An absorbent assembly 20 can be positioned between the top sheet layer 16 and the back sheet layer 18. The absorbent assembly 20 can be positioned beneath the fluid intake layer 52 in the Z-direction 28 of the absorbent article 10 as seen in FIG. 3. The absorbent assembly 20 can generally be any single layer structure or multiple layer components, which can demonstrate some level of compressibility, conformability, and capability of absorbing and retaining liquids and other body exudates. Additionally, the absorbent assembly 20 can provide additional capacity to absorb and retain body exudates such as menses. In various embodiments, the absorbent assembly can be formed from a variety of different materials and can contain any number of desired layers. For example, the absorbent assembly 20 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of a wood pulp fluff can be identified with the trade designation NB 416, available from Weyerhaeuser Corp., and is a bleached, highly absorbent wood pulp containing primarily soft wood fibers.

In various embodiments, if desired, the absorbent assembly 20 can include an optional amount of superabsorbent material. Examples of suitable superabsorbent material can include poly(acrylic acid), poly(methacrylic acid), poly (acrylamide), poly(vinyl ether), maleic anhydride copolymers with vinyl ethers and α-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent assembly 20 in any amount as desired.

Regardless of the combination of absorbent materials used in the absorbent assembly 20, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The shape of the absorbent assembly 20 can vary as desired and can comprise any one of various shapes including, but not limited to, triangular, rectangular, dog-bone and elliptical shapes. In various embodiments, the absorbent assembly 20 can have a shape that generally corresponds with the overall shape of the absorbent article 10 as illustrated herein. The dimensions of the absorbent assembly 20 can be substantially similar to those of the absorbent article 10, however, it will be appreciated that the dimensions of the absorbent assembly while similar, will often be less than those of the overall absorbent article 10, in order to be adequately contained therein.

By way of example, suitable materials and/or structures for the absorbent assembly 20 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al., each of which is hereby incorporated by reference thereto in its entirety.

As described above, in various embodiments, an absorbent assembly 20 can be a single layer structure and can include, for example, a matrix of cellulosic fluff and superabsorbent material (not shown). In various embodiments, such as illustrated herein, an absorbent assembly 20 can have at least two layers of material, such as, for example, an upper absorbent layer 88 and a lower absorbent layer 90. The upper absorbent layer 88 is positioned between the lower absorbent layer 90 and the fluid intake layer 52. The lower absorbent layer 90 is positioned between the upper absorbent layer 88 and the back sheet 18. In various embodiments, the two layers can be identical to each other (not shown). In various embodiments, the two layers can be different from each other as illustrated in FIG. 3. In such embodiments, the two layers can provide the absorbent article 10 with different absorption properties as deemed suitable. In various embodiments, the upper absorbent layer 88 of the absorbent assembly 20 may be constructed of an airlaid material and the lower absorbent layer 90 of the absorbent assembly 20 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

The absorbent assembly 20 defines an absorbent assembly length 92 in the longitudinal direction 24 (FIG. 2), an absorbent assembly width 94 (FIG. 4) in the lateral direction 26, and an absorbent assembly thickness 96 in the Z-direction 28 (FIG. 4). The upper absorbent layer 88 defines an upper absorbent layer length 98 in the longitudinal direction 24 (FIG. 2), an upper absorbent layer width 100 in the lateral direction 26 (FIG. 4), and an upper absorbent layer thickness in the Z-direction 28. Optionally, the upper absorbent layer length 98 is 180 to 300 mm, 190 to 260 mm, or 200 to 230 mm. Optionally, the upper absorbent layer width 100, as measured at the lateral centerline 31, is 40 to 80 mm, 50 to 70 mm, or 60 to 65 mm.

The lower absorbent layer 90 defines a lower absorbent layer length 104 in the longitudinal direction 24 (FIG. 2), a lower absorbent layer width 100 in the lateral direction 26 (FIG. 4), and a lower absorbent layer thickness in the Z-direction 28. Optionally, the lower absorbent layer length 104 is 140 to 250 mm, 150 to 225 mm, or 170 to 190 mm. Optionally, the lower absorbent layer width 106, at the lateral centerline 31, is 30 to 70 mm, 40 to 60 mm, or 40 to 50 mm.

Optionally, the upper absorbent layer width 100 is greater than the lower absorbent layer width 106. Optionally, the upper absorbent layer width 100 is greater than the fluid intake layer width 70. Optionally, the upper absorbent layer length 98 is greater than the fluid intake layer length 68. Optionally, the upper absorbent layer length 98 is greater than the lower absorbent layer length 104. Optionally, the fluid intake layer length 68 is less than the lower absorbent layer length 104. Optionally, the fluid intake layer width 70 is less than the lower absorbent layer width 106.

The back sheet layer 18 is generally liquid impermeable and is the portion of the absorbent article 10 which faces the garment of the wearer and generally defines the garment-facing surface 14 of the absorbent article 10. The back sheet layer 18 can permit the passage of air or vapor out of the absorbent article 10 while still blocking the passage of liquids. Any liquid impermeable material may generally be utilized to form the back sheet layer 18. The back sheet layer 18 can be composed of a single layer or multiple layers, and these one or more layers can themselves comprise similar or different materials. Suitable material that may be utilized can be a microporous polymeric film, such as a polyolefin film of polyethylene or polypropylene, nonwovens and nonwoven laminates, and film/nonwoven laminates. The particular structure and composition of the back sheet layer 18 can be selected from various known films and/or fabrics with the particular material being selected as appropriate to provide the desired level of liquid barrier, strength, abrasion resistance, tactile properties, aesthetics and so forth. In various embodiments, a polyethylene film can be utilized that can have a thickness in the range of from about 0.2 or 0.5 mils to about 3.0 or 5.0 mils. An example of a back sheet layer can be a polyethylene film such as that obtainable from Pliant Corporation, Schaumburg, Ill., USA. Another example can include calcium carbonate-filled polypropylene film. In still another embodiment, the back sheet layer 18 can be a hydrophobic nonwoven material with water barrier properties such as a nonwoven laminate, an example of which can be a spunbond, meltblown, meltblown, spunbond, four-layered laminate. The back sheet layer 18 can, therefore, be of a single or multiple layer construction, such as of multiple film layers or laminates of film and nonwoven fibrous layers. Suitable back sheet layers 18 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

Optionally, the absorbent article may include one or more lateral stiffeners 110. The lateral stiffeners 110 may be applied along the side edges 58, 60 of the fluid intake layer 52 as illustrated in FIG. 2. The lateral stiffeners 110 positioned along the side edges 58, 60 of the fluid intake layer 52 can transfer compressive forces applied by the legs at the central portion 36 of the absorbent article 10 to other portions of the absorbent article 10 where tenting and/or bending is desired. For example, the lateral stiffeners 110 may transfer compressive forces applied by the legs at the central portion 36 to the rear portion 34 of the absorbent article 10 where dynamic conformance to the wearer's body is desired.

The lateral stiffeners 110 can be produced by adding a stiff material, embossing, folding, pleating, bonding, and the like, and combinations thereof. Optionally, the lateral stiffeners 110 may be produced by embossing one or more elements of the absorbent article 10, such as the absorbent assembly 20. Likewise, the lateral stiffeners 110 can be produced by applying lines of hot melt adhesive or plastic strips. The lateral stiffeners 110 may be created by folding one or more elements of the absorbent article 10, like the liner and/or the back sheet 18. Stiff attachment means, such as hook and loop fastener strips, may act as lateral stiffeners or may add stiffness to the lateral stiffeners 110.

Optionally, the absorbent article 10 may include a first lateral stiffener 112 extending along a first side edge 58 of the fluid intake layer 52. Optionally, the absorbent article 10 may include a second lateral stiffener 114 extending along a second side edge 60 of the fluid intake layer 52. Optionally, the first lateral stiffener 112 and/or the second lateral stiffener 114 may be any suitable structure that provides rigidity to the absorbent article 10. Optionally, the first lateral stiffener 112 and/or the second lateral stiffener 114 may be embossments in the absorbent assembly 20. Optionally, the first lateral stiffener 112 and/or second lateral stiffener 114 may be embossments in the upper absorbent layer 88 of a multi-layered absorbent assembly 20 as illustrated in FIG. 4. Optionally, the first lateral stiffener 112 and/or the second lateral stiffener 114 may be embossments in both the upper absorbent layer 88 and the lower absorbent layer 90 (not illustrated).

Optionally, the first lateral stiffener 112 may extend along a majority of the fluid intake layer 52 first side edge 58. Optionally, the second lateral stiffener 114 may extend along a majority of the fluid intake layer 52 second side edge 60. Optionally, the first lateral stiffener 112 may extend beyond the first side edge 58 of the fluid intake layer 52 as illustrated in FIG. 1. Optionally, the second lateral stiffener 114 may extend beyond the second side edge 60 of the fluid intake layer 52 as illustrated in FIG. 1.

Optionally, the absorbent article 10 may include one or more flexures 116 positioned in the rear portion 34. The relative position of the flexures 116 is illustrated in FIG. 1. Additionally, details of the flexures 116 can be seen in FIG. 6, which is a magnified view of the area of FIG. 1 bound by the dot-dash rectangle 6. Flexures 116 help initiate and influence shaping of the absorbent article 10 into a tented configuration in the rear portion 34. The flexures 116 create different bend resistances across the absorbent article 10.

The flexures 116 can be created by physical discontinuities in the absorbent article 10 and/or elements of the absorbent article. For example, the flexures 116 can be created by pre-folding, scoring, indenting, perforating, embossing, bonding, or combinations thereof. Optionally, the flexures 116 can be created by scoring, folding, indenting, perforating, embossing, or bonding one or more layers of the absorbent assembly 20. Flexures 116 may also be created with changes in elevation and/or density to the absorbent article 10 and/or elements of the absorbent article. Optionally, the flexures 116 help initiate and regulate dynamic movement in the rear portion 34 of the absorbent article 10.

Optionally, the absorbent article 10 may include a first flexure 118 in the rear portion 34 of the absorbent article 10. Optionally, the first flexure 118 may extend in a direction generally parallel to the longitudinal centerline 30 as illustrated in FIG. 1. The first flexure 118 defines a front point 120 and a rear point 122 as illustrated in FIG. 6. Optionally, the first flexure 118 may be generally aligned with the maximum length 86 of the rearward-facing arch 84 as illustrated.

Optionally, the absorbent article 10 may include a second flexure 126 in the rear portion 34 of the absorbent article 10. The second flexure 126 may be spaced laterally outward from the first flexure 118 in a first direction 128. The second flexure 126 defines a first side portion 130 of the absorbent article 10. The first side portion 130 is positioned laterally outward from the second flexure 126 in the first direction 128 as illustrated in FIG. 1. The second flexure 126 defines a front point 132 and a rear point 134 as illustrated in FIG. 6.

Optionally, the absorbent article 10 may include a third flexure 138 in the rear portion 34 of the absorbent article 10. The third flexure 138 may be spaced laterally outward from the first flexure 118 in a second direction 140. The second direction 140 is opposite the first direction 128. The third flexure 138 defines a second side portion 142 of the absorbent article 10. The second side portion 142 is positioned laterally outward from the third flexure 138 in the second direction 140 as illustrated in FIG. 1. The third flexure 138 defines a front point 144 and a rear point 146 as illustrated in FIG. 6.

The second flexure 126 and the third flexure 138 define a dynamic region 150 of the absorbent article 10 there between. The second flexure 126 and the first flexure 118 define a first side 152 of the dynamic region 150. The third flexure 138 and the first flexure 118 define a second side 154 of the dynamic region 150 as illustrated in FIG. 6.

Optionally, the second flexure 126 and/or the third flexure 138 may be oriented in a direction generally parallel to the longitudinal centerline 30 (not shown). Alternately, the second flexure 126 and/or the third flexure 138 may be positioned at an angle relative to the longitudinal centerline 30. For example, in some embodiments, the second flexure 126 and/or the third flexure 138 may diverge rearward at a first angle 156 relative to the longitudinal centerline 30 as illustrated in FIG. 6. Optionally, the first angle 156 may be 1 to 10 degrees, 2 to 7 degrees, or 3 to 5 degrees relative to the longitudinal centerline 30. Optionally, the second flexure 126 and/or the third flexure 138 may be positioned at an angle relative to the longitudinal centerline 30 and may be generally aligned with one or more haunches 182. For example, both the second flexure 126 and the third flexure 138 are aligned with the haunches 182 as illustrated in FIG. 6.

Optionally, the second flexure 126 may include a first return portion 158 converging rearward at a second angle 160 relative to the longitudinal centerline 30. Optionally, the third flexure 138 may include a second return portion 162 converging rearward at the second angle 160 relative to the longitudinal centerline 30 as illustrated in FIG. 6. It is believed that the first return portion 158 and/or the second return portion 162 helps to form the tented configuration in the rear portion 34 of the absorbent article 10 by helping transfer lateral compression into upward tent formation.

Optionally, the first flexure 118, the second flexure 126, and the third flexure 138 are embossments in the absorbent assembly 20. Optionally, the first flexure 118, the second flexure 126, and/or the third flexure 138 are embossments in the upper absorbent layer 88 of a multi-layered absorbent assembly 20.

Optionally, the first flexure 118, the second flexure 126, and/or the third flexure 138 extend under the fluid intake layer 52 (not illustrated). Optionally, the first flexure 118, the second flexure 126, and/or the third flexure 138 terminate at respective front points 120, 132, and 144 proximate the rearward-facing arch 84 of the fluid intake layer 52 as illustrated in FIG. 6. The longitudinal spacing between the respective front points 120, 132, and 144 and the rearward-facing arch 84 defines a transition zone 184 having a transition zone length 186. Optionally, the transition zone 184 provides a region of lower density as compared to the flexures 116 and the fluid intake layer 52.

Optionally, the absorbent article 10 includes a fastening system 166 as best illustrated in FIG. 5. The fastening system 166 may be adapted to secure the absorbent article 10 to the undergarment of the wearer. Specifically, the fastening system 166 may include one or more separate fasteners 168 positioned in any suitable arrangement on the garment-facing surface 14 of the back sheet 18. Optionally, the fastening system 166 may include a first fastener 170 attached to the garment-facing surface 14 of the back sheet 18 in the first side portion 130 and a second fastener 172 attached to the garment-facing surface 14 of the back sheet 18 in the second side portion 142. Optionally, the central portion 174 of the garment-facing surface 14 of the back sheet 18 is substantially free of fasteners in the rear portion 34. Optionally, the central portion 174 may have a width 175 in the lateral direction 26 of 15 to 60 mm, 20 to 50 mm, or 30 to 45 mm. When the central portion 174 of the garment-facing surface 14 of the back sheet 18 is substantially free of fasteners, the central portion 174 is substantially unattached to the undergarment of the wearer and can move in response to the alternating movement of the legs thereby isolating the central portion 36 and the front portion 32 of the absorbent article 10 and allowing these regions to stay in place during movement of the wearer.

In various embodiments, the fasteners 168 may include any suitable attachment means, such as, adhesive, cohesive, hooks, snaps, clips, or the like, or combinations thereof. Optionally, the first fastener 170 may be a mechanical hook material attached to the garment-facing surface 14 of the back sheet 18 in the first side portion 130 and the second fastener 172 may be a mechanical hook material attached to the garment-facing surface 14 of the back sheet 18 in the second side portion 142. Optionally, the first fastener 170 may be an adhesive attached to the garment-facing surface 14 of the back sheet 18 in the first side portion 130 and the second fastener 172 may be an adhesive attached to the garment-facing surface 14 of the back sheet 18 in the second side portion 142.

Optionally, the first fastener 170 and/or the second fastener 172 may be continuous materials that extend from the front portion 32 of the absorbent article 10, through the central portion 36, and into the rear portion 34 as illustrated in FIG. 5. Optionally, the first fastener 170 and/or the second fastener 172 may be continuous hook materials that extend from the front portion 32 through the central portion 36 and into the rear portion 34. Optionally, the first fastener 170 and/or the second fastener 172 may be continuous adhesive materials that extend from the front portion 32 of the absorbent article 10, through the central portion 36, and into the rear portion 34. Optionally, the first fastener 170 and/or the second fastener 172 may be separate and distinct materials positioned only in the rear portion 34.

Optionally, the first fastener 170 may be applied to the garment-facing surface 14 of the back sheet 18 in the first side portion 130 and at an angle 156 relative to the longitudinal centerline 30 (not shown). Optionally, the second fastener 172 may be applied to the garment-facing surface 14 of the back sheet 18 in the second side portion 142 and at an angle 156 relative to the longitudinal centerline 30 (not shown). Optionally, the first fastener 170 may be applied at an angle 156 relative to the longitudinal centerline 31 to be generally parallel with the second flexure 126 (not shown). Optionally, the second fastener 172 may be applied at an angle 156 relative to the longitudinal centerline 31 to be generally parallel with the third flexure 138 (not shown).

Optionally, the absorbent article 10 may include attachment wings 176 extending from the lateral side edges 44, 46 as illustrated in FIGS. 1 and 4. The wings 176 can be constructed from materials described above with respect to the top sheet layer 16 and the back sheet layer 18. In various embodiments, the wings 176 can comprise an extension of a layer of material within the top sheet layer 16 and/or the back sheet layer 18. By way of example, the wings 176 can be formed by an extension of the top sheet layer 16 and the back sheet layer 18. Such wings can be integrally formed with the main portion of the absorbent article 10. Alternatively, the wings 176 can be formed independently and separately attached to a central portion 36 of the absorbent article 10 (not illustrated). Wings 176 that are made independent of the other components of the absorbent article 10 can be bonded to a portion of the top sheet layer 16 and/or back sheet layer 18. Examples of processes for manufacturing absorbent articles 10 and wings 176 include, but are not limited to, those described in U.S. Pat. No. 4,059,114 to Richards, U.S. Pat. No. 4,862,574 to Hassim, et al., U.S. Pat. No. 5,342,647 to Heindel, et al., U.S. Pat. No. 7,070,672 to Alcantara, et al., U.S. Publication No., 2004/0040650 to Venturino, et al., and international publication WO1997/040804 to Emenaker, et al., each of which are hereby incorporated by reference thereto in its entirety.

The wings 176 define a rear wing position 178 in the longitudinal direction 24 (FIG. 1). Optionally, the rear wing position 178 may be closer to the front edge 48 of the absorbent article 10 than the front points 120, 132, and/or 144 (FIG. 6).

Figure 8:
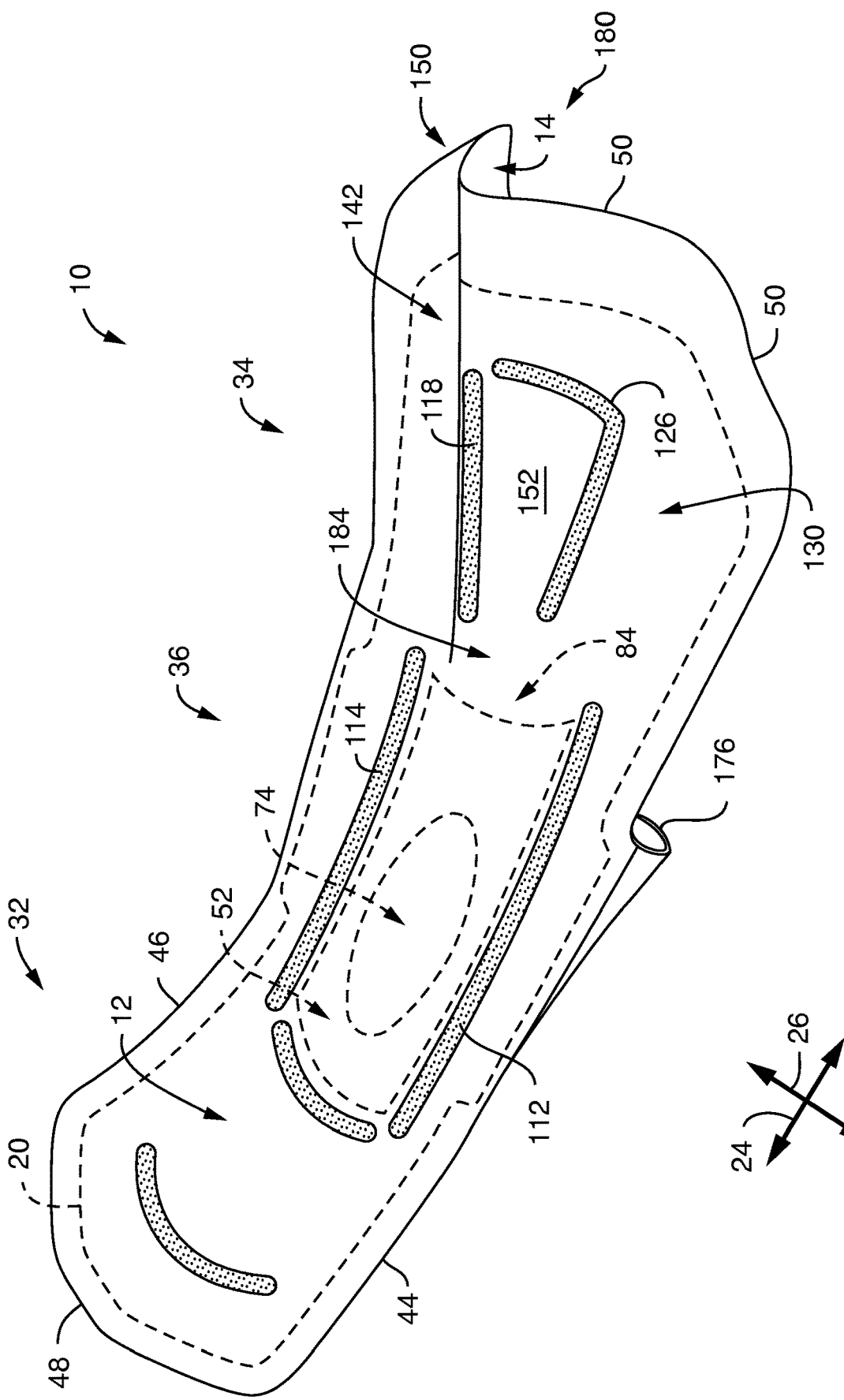
FIG. 8 is a perspective view of the absorbent article of FIG. 1 in a tented configuration.

Referring now to FIG. 8, the absorbent article 10 of FIG. 1 is illustrated in a tented configuration 180. The tented configuration 180 is formed in the rear portion 34 when the absorbent article 10 is subjected to lateral compressive force. The tented configuration 180 is formed relative to the first flexure 118, the second flexure 126, and the third flexure 138 (not visible in this view). The tented configuration 180 is adapted to conform to the perineal region posterior to the vulva for the purpose of intercepting fluid moving along the skin and/or preventing fluids from following the body beyond the vulva region. The tented configuration 180 includes the back sheet 18, the absorbent assembly 20, the fluid intake layer 52, and the top sheet 16. The tented configuration 180 is shaped by the rearward-facing arch 84 of the fluid intake layer 52, the first flexure 118, the second flexure 126, and the third flexure 138. The tented configuration 180 is dynamic due to the lack of attachment (panty to pad) in the central portion 174 of the back sheet 18. Attempts to achieve reliable upward deformation and the desired tented configuration 180 without the rearward-facing arch 84 have not been satisfactory. A rounded or square rear portion of the fluid intake layer does not reliably produce upward deformation and the tented configuration 180. The first flexure 118 is believed to act as a lever to assist in lifting the tented configuration 180 to provide contact against the perineum and posterior vulva. The lifting force is generated by the reciprocating motion of the legs. This reciprocating motion alternately pumps the first side 152 of the dynamic region 150 and the second side 154 (not visible in this view) of the dynamic region 150 towards the gluteal cleft. Generally, the compressive force of the legs alternates when walking or running. In these situations, the compressive force alternates between the two sides of the absorbent article 10. The compressive force pushes alternately on the first lateral stiffener 112 and the second lateral stiffener 114. The compressive force is transferred to the dynamic region 150 in the rear portion 34 of the absorbent article. The first side 152 of the dynamic region acts as a plane that works in conjunction with the first lateral stiffener 112 to push the first side 152 up into the tented configuration. Likewise, the second side 154 of the dynamic region 150 acts as a plane that works in conjunction with the second lateral stiffener 114 to push the second side 154 up into the tented configuration 180 as illustrated in FIG. 8. The first side 152 and the second side 154 are free to move in response to the lateral forces because the central portion 174 of the back sheet 18 is substantially free of fasteners. Because the first fastener 170 is positioned in the first side portion 130, the first side 152 is pulled back out when the compressive force is removed. Likewise, because the second fastener 172 is positioned in the second side portion 142, the second side 154 is pulled back out when the compressive force is removed. This configuration allows the base of the tented configuration to expand and contract when the wearer walks and allows the peak of the tented configuration to remain upright when the wearer walks.

While the invention has been described in detail with respect to specific embodiments thereof, it will be appreciated that those skilled in the art, upon attaining understanding of the foregoing will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. An absorbent article comprising,
a top sheet,
a back sheet,
an absorbent assembly positioned between the back sheet and the top sheet, and
a fluid intake layer positioned between the absorbent assembly and the top sheet, the fluid intake layer defining a fluid intake layer length in a longitudinal direction and the absorbent article defining an absorbent article length in the longitudinal direction, the fluid intake layer length being 30-60% the absorbent article length, the fluid intake layer also defining an outer perimeter, the outer perimeter having a rearward-facing arch located in a back portion of the fluid intake layer.

2. The absorbent article of claim 1 further comprising, a first lateral stiffener extending along a first side edge of the fluid intake layer, a second lateral stiffener extending along a second side edge of the fluid intake layer, and a first flexure in a rear portion of the absorbent article, the first flexure extending in a direction generally parallel to a longitudinal centerline.

3. The absorbent article of claim 1 further comprising, a first flexure in a rear portion of the absorbent article, the first flexure extending in a direction generally parallel to a longitudinal centerline, a second flexure in the rear portion of the absorbent article spaced laterally outward in a first direction from the first flexure, the second flexure defining a first side portion of the absorbent article laterally outward in the first direction from the second flexure and a third flexure in the rear portion of the absorbent article spaced laterally outward in a second direction from the first flexure, the second direction being opposite the first direction, the third flexure defining a second side portion of the absorbent article laterally outward in the second direction from the third flexure, the second and third flexures defining a central portion of the absorbent article therebetween.

4. The absorbent article of claim 3 further comprising, a first fastener attached to the garment-facing surface of the back sheet in the first side portion, and a second fastener attached to the garment-facing surface of the back sheet in the second side portion, wherein the central portion of the garment-facing surface of the back sheet is substantially free of fasteners.

5. The absorbent article of claim 3 wherein the second flexure and the third flexure diverge rearward relative to the longitudinal centerline and wherein the first flexure, the second flexure, and the third flexure terminate at front points proximate the rearward-facing arch of the fluid intake layer.

6. The absorbent article of claim 3 wherein the first flexure, the second flexure, and the third flexure are embossments in the absorbent assembly.

7. The absorbent article of claim 4 wherein the first fastener is a mechanical hook material attached to the garment-facing surface of the back sheet in the first side portion and the second fastener is a mechanical hook material attached to the garment-facing surface of the back sheet in the second side portion.

8. The absorbent article of claim 4 wherein the first fastener is an adhesive attached to the garment-facing surface of the back sheet in the first side portion and the second fastener is an adhesive attached to the garment-facing surface of the back sheet in the second side portion.

9. The absorbent article of claim 1 wherein the fluid intake layer is an airlaid material comprising bi-component fibers and pulp fibers and the rearward-facing arch defines a length dimension in the longitudinal direction of 7-15 mm.

* * * * *